US008979867B2

(12) United States Patent
Peyman

(10) Patent No.: US 8,979,867 B2
(45) Date of Patent: Mar. 17, 2015

(54) VITREOUS CUTTER

(76) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 13/242,323

(22) Filed: Sep. 23, 2011

(65) Prior Publication Data
US 2013/0079806 A1 Mar. 28, 2013

(51) Int. Cl.
A61B 17/34 (2006.01)
A61F 9/007 (2006.01)
A61B 17/32 (2006.01)
A61B 19/00 (2006.01)

(52) U.S. Cl.
CPC ............. *A61F 9/00736* (2013.01); *A61B 17/32* (2013.01); *A61B 19/5202* (2013.01); *A61B 2217/005* (2013.01)
USPC .......................................... 606/107; 606/185

(58) Field of Classification Search
USPC ............................ 606/166, 185, 107; 600/249
See application file for complete search history.

(56) References Cited

U.S. PATENT DOCUMENTS

| 4,019,514 A * | 4/1977 | Banko ............................. 604/31 |
| 4,099,529 A | 7/1978 | Peyman |
| 4,551,129 A * | 11/1985 | Coleman et al. ................ 604/21 |
| 5,591,160 A * | 1/1997 | Reynard .......................... 606/15 |
| 5,690,663 A * | 11/1997 | Stephens ........................ 606/185 |
| 5,725,514 A * | 3/1998 | Grinblat et al. ............... 604/294 |
| 6,936,053 B1 * | 8/2005 | Weiss ............................. 606/107 |
| 7,783,346 B2 * | 8/2010 | Smith et al. ..................... 604/21 |
| 8,231,544 B2 * | 7/2012 | Mark ............................. 600/566 |
| 2007/0225727 A1 * | 9/2007 | Matsuhisa et al. ............. 606/107 |
| 2008/0086160 A1 * | 4/2008 | Mastri et al. .................. 606/185 |
| 2011/0112377 A1 * | 5/2011 | Papac et al. ................... 600/249 |
| 2011/0230728 A1 * | 9/2011 | Artsyukhovich et al. ..... 600/249 |
| 2012/0035425 A1 * | 2/2012 | Schaller ........................ 600/249 |
| 2012/0083793 A1 * | 4/2012 | Foster ........................... 606/107 |

* cited by examiner

Primary Examiner — Thomas McEvoy
Assistant Examiner — Julie A Szpira
(74) Attorney, Agent, or Firm — The Law Office of Patrick F. O'Reilly III, LLC

(57) ABSTRACT

A vitrectomy or needle made of a hard resistance metal glass alloy. The wall of the outer tubing or the entire needle can be illuminated when connected to a light source. The instrument, when inserted inside the tissue or the eye, provides illumination, thereby illuminating the surrounding tissue structure and eliminating the need for additional internal or external illumination.

16 Claims, 4 Drawing Sheets

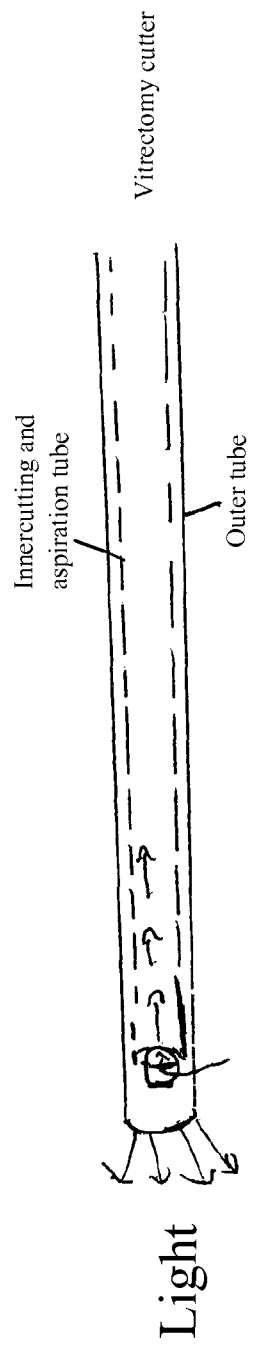

VITREOUS CUTTER

BACKGROUND OF THE INVENTION

I. Field of the Invention

The present invention is related to vitreous cutters that are used in vitrectomy procedures to remove vitreous from the eye. In particular, the present invention is related to vitreous cutters having a light source to illuminate a portion of the eye.

II. Description of the Related Art

Vitrectomy is a procedure in which the degenerative vitreous is removed to clear the opaque optical media (vitreous) or to eliminate traction on the retina which produces a localized or generalized retinal detachment. The function of a vitrectomy instrument is described in patent U.S. Pat. No. 4,099,529 to Peyman, the entire contents of which are herein incoprporated by reference. That is, generally, the cutting part includes concentric tubing. An inner tube serves as the inner cutting edge of the instrument and has an oscillating action, and the opening in the tightly fit outer tube serves as the outer edge of the cutting. The vitreous is aspirated through a small opening close to the tip of the outer stationary tube, i.e., the outer cutting edge. The aspiration force, generated by a pump, when applied through the inner tube draws the vitreous through the outer hole toward the inside of the inner tube. The oscillation of the inner tube cuts the vitreous/tissue trapped in the opening of the outer tube and is aspirated into a reservoir. To balance the intraocular pressure, physiologic saline solution is infused through a second independent "infusion tube" placed inside the eye cavity through a separate incision in the eye wall.

During the procedure the vitreous cavity is illuminated through a separate fiber optic brought inside the eye through a third incision. The diameter of the vitrectomy cutting cutters varies between 20-23-25-27 gauge. The most desirous sizes are a 23 gauge, 25 gauge and 27 tubes because these sizes eliminate the need to close the incision in the eye wall by a suture and the smaller the instrument is, the less traumatic the surgery becomes.

There are several disadvantages of the conventional systems. First, there is a need for at least three incision for the cutter, infusion and the light sources. Second, the 25 gauge and 27 gauge tips, because of their size are too flexible inside the eye. That is, the slightest pressure that moves the eye during surgery also can bend the shaft of the cutter in one direction at the incision site while the inside portion of the shaft moves in another direction. This movement can be disturbing to an operator who does not expect motion in the opposite direction than which was intended and can cause injury to the fine structure of the lens or the retina. Third, in myopic eyes having a longer axial length than normal, a longer (36-38 mm) than normal shaft (e.g., 30 mm) is required. This makes the instrument flimsy and not desirable.

SUMMARY OF THE INVENTION

An object of the present invention is to provide vitrectomy cutters 1) with harder than stainless steel material that eliminate the short coming of the vitreous cutters; 2) that eliminate the need for addition incisions made for the fiber optic illumination by bringing the light through the shaft of the cutter; 3) that can be used as a needle for penetrating the tissue as a biopsy probe; and 4) one could have a combination of a probe for cutting, illumination and infusion in a single instrument that would have a 23-25 gauge diameter, and would not require an additional incision or suturing the entrance wound. This modification would eliminate all the above shortcomings of the conventional systems and would also provide an instrument with a longer shaft of up to 38 mm long or longer.

It is a further object of the present invention to create a 30 gauge cutter made of two concentric tubes. The outer tube has an opening in its distal end of its body through which vitreous or tissue is aspirated inside the inner tube. The inner tube simultaneously has an osculating and cutting action. The cut and aspirated matter is removed through the inner tube connected with a vacuum system. These and other embodiments can be used also for obtaining tissue biopsy from not only the intraocular tumors but other tumors such as breast, prostate etc.

The objects of the present invention may be accomplished by a vitrectomy cutter including a needle with a body and a tip, the needle being made from one of metal glass and amorphous glass, and an illumination device disposed inside the needle body, such that the illumination device is capable of providing illumination to an entire portion of the eye through at least one of the tip of said needle and the body of the needle.

BRIEF DESCRIPTION OF THE DRAWINGS

FIG. 4b illustrates an embodiment of the present invention in which the needle for the cutter is illuminated and is partially coated, so that only the tip shines through.

FIG. 5 illustrates a vitreous cutter including two tubes.

DETAILED DESCRIPTION OF THE INVENTION

Figure 1:
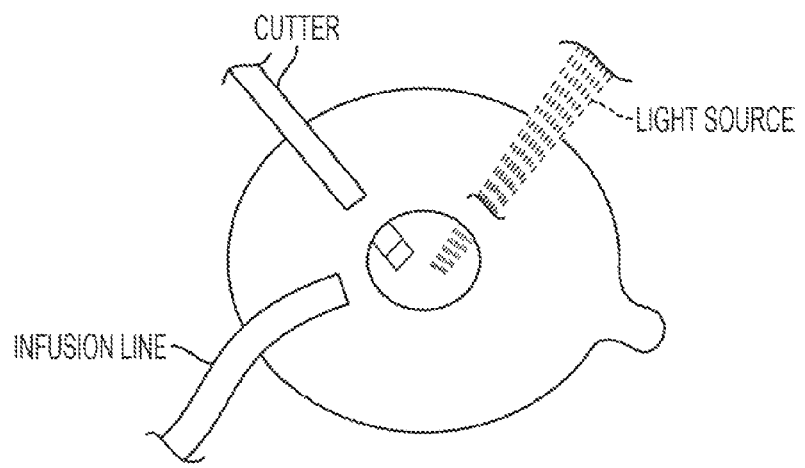
FIG. 1 illustrates a conventional vitrectomy that requires three independent incisions for different size of the instruments (cutter, infusion, illumination)
Figure 2:
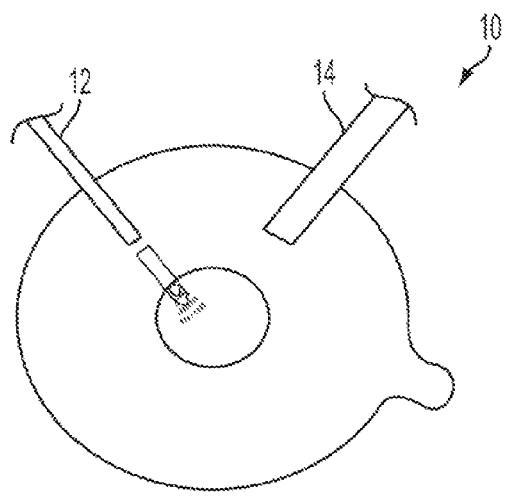
FIG. 2 illustrates an embodiment of the present invention having three functions using two small sized cutters, 20-30 gauge.
Figure 3A:
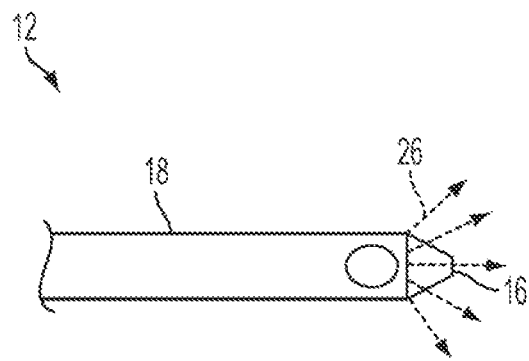
FIGS. 3a and 3b show embodiments of the present invention having a modified tip for the cutter for penetration in the tissue (FIG. 3a having illumination and FIG. 3b without illumination)
Figure 3B:
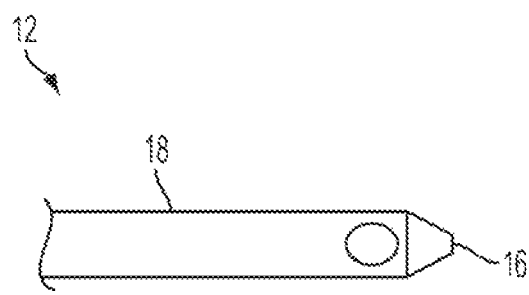
Figure 4A:
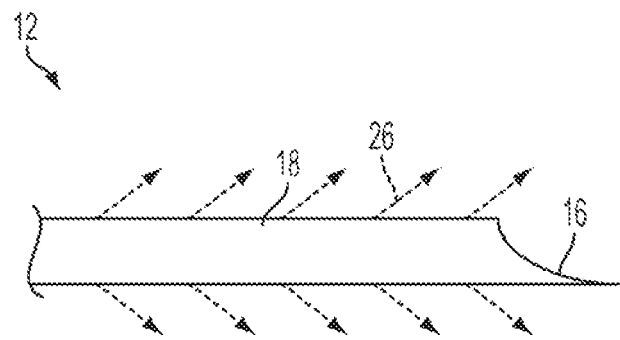
FIG. 4a illustrates an embodiment of the present invention in which the needle for the cutter is illuminated and is uncoated.
Figure 4B:
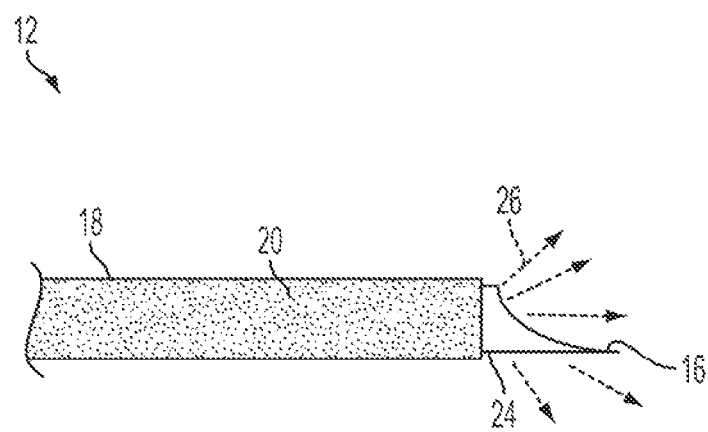

As shown in FIGS. 2-4b, the present invention is a vitrectomy method using a system 10 that includes a cutter device or instrument 12 with illumination and an infusion line 14. The instrument 12 includes a tip 16 and body 18. Such a system enables fewer incisions to be made in the eye, relative to conventional systems. In one embodiment, the tip 16 of the cutter device 12 can be made to be like standard needles used for vein puncture to draw blood from a subject. In another embodiment, a simple needle can be created with these characteristics for infusion or drawing blood from a subject.

The instrument can be illuminated by any standard illuminating system providing the needed light intensity. The illumination device can be disposed inside or outside the need or in any suitable position relative to the needle. The illumination device is preferably of the connected to the needle/cutter at a site that does not enter the body. It can either illuminate the entire needle/cutter or the outer surface of the instrument can be coated with a thin layer of black material 20 (see FIG. 4b) leaving only the tip 16 or an area 24 adjacent the tip free to permit the light 26 to exit the instrument. The illumination permits visualization of the tissue, once the needle has penetrated a soft tissue and can be followed by observing its path and position of the needle tip. This eliminates guessing how far a needle has penetrated the tissue.

It is understood that the tip of the instrument can be made any for any desired shape round, pointed, sharp blade etc or any length.

The cutter can be made from various composites such as metal glass, amorphous glass or similar alloys such as palladium alloy and zirconium alloy, or any other suitable material. These compounds are tougher than presently used stainless steel for conventional vitrectomy cutters or needles. These compounds are also transparent to visible light from 400-800 nm, such that it is possible to direct the light for visualization through the body of the cutter without increasing the diameter of the instrument or the need for additional incision for a fiber optic. Similarly, aluminum nitryloxyde is a transparent polycrystalline ceramic structure composed of aluminum and oxygen. This compound is harder than fused silica glass and sapphire or magnesium aluminum. It is light weight and resistant to damage by oxidation or radiation. The manufacturing technique is known and is as with conventional ceramic powder.

It should be understood that the invention is not limited to the described material but all compounds that can provide the hardness and light transparency and are not brittle.

What is claimed is:

1. A vitrectomy cutter, comprising:
    a needle with a body and a closed end tip, said body of said needle including a sidewall extending in an axial direction from said closed end tip, said body of said needle defining a linear passageway closed at a distal end by said closed end tip, said needle coated with a black material and being configured to cut vitreous or tissue and being made from a compound that is transparent to visible light, wherein the compound is transparent to visible light from 400-800 nm, and wherein the compound comprises one of: metal glass, amorphous glass, palladium alloy, zirconium alloy and aluminum nitrloxyde; and
    an illumination device connected to said body of said needle, such that said illumination device is capable of providing illumination to an inside portion of an eye through at least one of said closed end tip of said needle and said body of said needle,
    wherein the needle includes an opening disposed in said sidewall of said body, said opening being disposed proximate to said closed end tip of said needle, and said opening being configured to enable cutting of the vitreous or the tissue.

2. The vitrectomy cutter according to claim 1 wherein said compound that is transparent to visible light is one of metal glass and amorphous glass.

3. The vitrectomy cutter according to claim 1 wherein said illumination device is connected to said body of said needle at a portion of said needle that does not enter the eye.

4. The vitrectomy cutter according to claim 1 wherein said illumination device is disposed inside said body of said needle.

5. The vitrectomy cutter according to claim 1 wherein said compound is aluminum nitryloxyde.

6. The vitrectomy cutter according to claim 1 wherein said needle is configured to cut the vitreous or the tissue such that the vitreous or the tissue is capable of being removed.

7. The vitrectomy cutter according to claim 1 wherein said needle is an outer tube, and said vitrectomy cutter further comprises an inner tube, and
    wherein said inner tube is configured to oscillate so as to be capable of cutting the vitreous or the tissue that enters the opening in said outer tube.

8. The vitrectomy cutter according to claim 7 wherein said inner tube is configured to enable the cut vitreous or the cut tissue to be removed.

9. A vitrectomy cutter, comprising:
    a needle with a body and a closed end tip, said body of said needle including a sidewall extending in axial direction from said closed end tip, said body of said needle defining a linear passageway closed at a distal end by said closed end tip, said needle coated with a black material and being configured to cut vitreous or tissue and being made from a compound that is transparent to visible light, wherein the compound is transparent to visible light from 400-800 nm, and wherein the compound comprises one of: metal glass, amorphous glass, palladium alloy, zirconium alloy and aluminum nitrloxyde; said needle further including an opening disposed in said sidewall of said body, said opening being disposed proximate to said closed end tip of said needle, and said opening being configured to enable cutting of the vitreous or the tissue; and
    an illumination device connected to said body of said needle, such that said illumination device is capable of providing illumination to an inside portion of an eye through at least one of said closed end tip of said needle and said body of said needle, and through a portion of said needle that is adjacent to said opening disposed in said sidewall of said body.

10. The vitrectomy cutter according to claim 9 wherein said compound that is transparent to visible light is one of metal glass and amorphous glass.

11. The vitrectomy cutter according to claim 9 wherein said compound is aluminum nitryloxyde.

12. A vitrectomy cutter, comprising:
    a needle in the form of an outer tube with a body and a closed end tip, said body of said needle including a sidewall extending in axial direction from said closed end tip, said body of said needle coated with a black material and defining a linear passageway closed at a distal end by said closed end tip, said needle being configured to cut vitreous or tissue and being made from a compound that is transparent to visible light, wherein the compound is transparent to visible light from 400-800 nm, and wherein the compound comprises one of: metal glass, amorphous glass, palladium alloy, zirconium alloy and aluminum nitryloxyde; said needle further including an opening disposed in said sidewall of said body, said opening being disposed proximate to said closed end tip of said needle, and said opening being configured to enable cutting of the vitreous or the tissue;
    an inner tube arranged concentrically within said outer tube, said inner tube being configured to oscillate so as to be capable of cutting the vitreous or the tissue that enters said opening in said body of said outer tube; and
    an illumination device connected to said body of said needle, such that said illumination device is capable of providing illumination to an inside portion of an eye through at least one of said closed end tip of said needle and said body of said needle, and through a portion of said needle that is adjacent to said opening disposed in said sidewall of said body.

13. The vitrectomy cutter according to claim 12 wherein said compound that is transparent to visible light is one of metal glass and amorphous glass.

14. The vitrectomy cutter according to claim 12 wherein said compound is aluminum nitryloxyde.

15. The vitrectomy cutter according to claim 12 wherein said inner tube is configured to remove the cut vitreous or the cut tissue by applying an aspiration force to the cut vitreous or the cut tissue.

16. The vitrectomy cutter according to claim 15 wherein said aspiration force is configured to draw the cut vitreous or the cut tissue through said opening disposed in said sidewall of said body of said outer tube.

\* \* \* \* \*